United States Patent [19]

Okamoto et al.

[11] Patent Number: 5,290,961
[45] Date of Patent: Mar. 1, 1994

[54] PLATINUM COMPOUND AND PROCESS OF PREPARING SAME

[75] Inventors: Koji Okamoto; Yuko Hoshi; Chihiro Nakanishi, all of Kanagawa, Japan

[73] Assignee: Tanaka Kikinzoku Kogyo K.K., Japan

[21] Appl. No.: 3,306

[22] Filed: Jan. 12, 1993

[30] Foreign Application Priority Data

Jan. 13, 1992 [JP] Japan .................. 4-23219

[51] Int. Cl.$^5$ .................................. C07F 15/00
[52] U.S. Cl. .................................. 556/137
[58] Field of Search .......................... 556/137

[56] References Cited

U.S. PATENT DOCUMENTS 4,658,048 4/1987 Totani et al. .................. 556/137
4,661,516 4/1987 Brown et al. .................. 514/492

Primary Examiner—José G. Dees
Assistant Examiner—Porfirio Nazario-Gonzalez
Attorney, Agent, or Firm—Klauber & Jackson

[57] ABSTRACT

Disclosed herein are a platinum compound employed as raw material of medicines having carcinostatic effects, and a process of preparing the platinum compound. The platinum compound (I) substantially free from impurities can be prepared through a reaction between the corresponding dihalogen compound and an organic dibasic acid employing an iodine compound utilizing the difference of solubilities between the desired compound and the iodine compounds.

2 Claims, No Drawings

PLATINUM COMPOUND AND PROCESS OF PREPARING SAME

BACKGROUND OF THE INVENTION

The present invention relates to a platinum compound and a process of preparing the same.

Heretofore, compounds (I) and (II) have been known as platinum compounds having carcinostatic effects. The compound (I) has been obtained by means of the following procedures. At first, the compound (II) is prepared by reacting $K_2Pl(II)X_4$ (X is Cl or Br) with a 1,2-cyclohexanediamine isomer. A silver nitrate solution of two equivalents in respect to the compound (II) is added to a solution prepared by dissolving the compound (II) into water under boiling to precipitate chlorine or bromine as silver chloride or silver bromide which is then filtered off. To the filtrate is added an organic dibasic acid to obtain the desired compound (I).

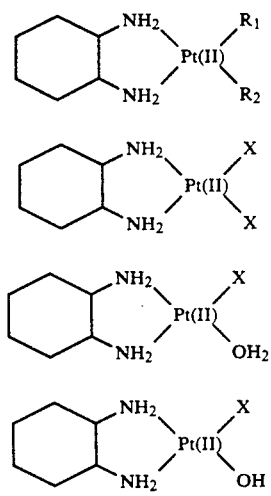

However, this preparation process possesses a disadvantage that many impurities such as the unreacted compound (II), compounds (III) and (IV) which are by-products of the compound (II) and an unreacted silver ion remain in the compound (I) prepared according to the above process.

One of the reasons the impurities are contaminated in the desired compound (I) is the low solubility of the compound (II) in water. For example, when the compound (II) is a chloride of a trans-1 isomer, its considerably low solubility in water is about 0.26 mg/ml and oven if dissolved under boiling, only about 0.5 mg/ml of the compound (II) dissolves. Because of the low solubility of the compound (II), it is quite difficult to completely dechlorinate the compound (II) from the viewpoint of its characteristics resulting in the contamination of the above impurities.

A remarkable problem also remains in the removal of the silver chloride formed as a result of the above reaction. The solubility of the silver chloride is relatively low so that almost all the silver chloride formed can be removed in ordinary conditions. However, in the above reaction, a large amount of water is required due to the low solubility of the compound (II) so that the complete removal of the silver chloride may be impossible in such a reaction employing a large amount of water.

This tendency becomes worse when the bromide is employed.

Many platinum compounds may possess physiologic activities such as cytotoxicity, and the contamination of the above unreacted compound (II) and the by-products (III) and (IV) is not allowed in the raw material for medicines having carcinostatic effects even if a trace amount. The unreacted silver ion which may exist in the medicines is regulated in a heavy metal test method, but no satisfactory value in connection with the silver ion has been obtained in conventional methods.

SUMMARY OF THE INVENTION

An object of the present invention is to provide a process of preparing a compound (I) which can be employed for raw material of a medicine having carcinostatic effects.

Another object of the invention is to provide a process of preparing a compound (I) which is not contaminated with such impurities as the above compounds (II), (III) and (IV) and an unreacted silver ion.

A further object of the invention is to provide the compound (I) substantially free from the above impurities.

The present invention has been made to overcome the above-mentioned drawbacks of the prior art. The objects can be attained by adding to a compound (II) a silver ion solution containing not less than two equivalents of silver in respect to the compound (II), removing silver chloride and/or silver bromide formed, adding to the solution sodium iodide and/or potassium iodide to covert the unreacted compound (II), the by-products of the compound (II) and an unreacted silver ion into their iodine compounds followed by the removal thereof and thereafter adding an organic dibasic acid thereto to form the platinum complex (I).

DETAILED DESCRIPTION OF THE INVENTION

In the above preparation process, after the removal, preferably the filtration of the silver chloride and/or the silver bromide, such impurities as the unreacted compound (II), the compounds (III) and (IV) are converted into the corresponding iodine compounds by adding sodium iodide and/or potassium iodide thereto. Since the solubility of these iodine compounds in water is remarkably low so as to make a large difference between the said solubility and that of the desired compound (I), the iodide compounds can be completely removed, for example, by filtration to provide the final desired compound (I) contaminated with substantially no impurities.

In the formula (I), $R_1$ and $R_2$ form with each other a circular group selected from the formulae (V), (VI), (VII), (VIII), (IX) and (X). In other words, $R_1$ and $R_2$ form with each other an aliphalic dibasic acid residue. Almost all the platinum compounds shown in the formula (I) and prepared in accordance with the process of the present invention possess carcinostatic effects which are not depressed because of no contamination with impurities.

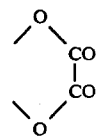

V

-continued

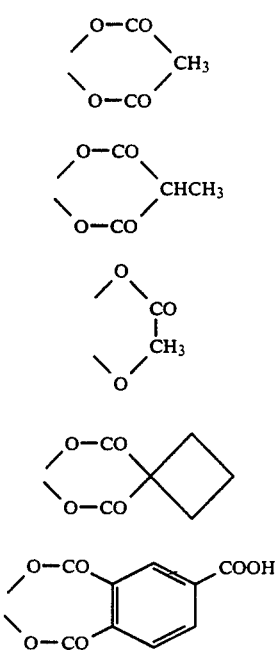

EXAMPLE

A preferred Example of this invention will be hereinafter described. Although a process of preparing ois-oxalate (trans-1-1,2-cyclohexanediamine) platinum (II) as a representative of the compound (I) will be illustrated, the Example does not intend to restrict the present invention.

EXAMPLE 562.5 g of potassium chloroplatinate and 154.8 g of trans 1-1,2-cyclohexanediamine were dissolved and mixed in 3.5 liters of water to obtain cake-like cis-dichloro (trans-1-1,2-cyclohexanediamine) platinum (II) without recrystallization with a yield of 96%. This compound was suspended in 5.7 liters of water to which was added a solution which had been prepared by dissolving 386.4 g of silver nitrate in 2.8 liters of water. After this solution was stirred in the dark at a room temperature for three days, most of the precipitate of the silver chloride was removed by filtration. After the filtrate was concentrated under a reduced pressure, a solution consisting of 45 ml of water and 3.85 g of potassium iodide dissolved therein was added followed by one hour stirring, and then active carbon was added. Silver iodido and iodine compounds of (II), (III) and (IV) then formed and the active carbon were completely removed by filtration. To the remaining filtrate was added 146.3 g of oxalic acid which was allowed to stand for two hours to obtain crude crystal of desired cis-oxalate (trans 1-1,2-cyclohexanediamine) platinum (II) with a yield of 80%. Then, 70 g of this crude crystal was dissolved under heating in 2.7 liters of water, filtered and cooled to a room temperature. The platinum crystal precipitated was collected by filtration and washed with a small amount of water. The crystal obtained was dried to obtain the desired platinum complex. These experiments were repeated five times of which yields were 49 g, 45 g, 50 g, 48 g and 47 g.

COMPARATIVE EXAMPLE

After the cake-like cis-dichloro (trans-1-1,2-cyclohexanediamine) platinum (II) was obtained under the same conditions as those of Example, this cake like substance was dissolved in 5.7 liters of water under boiling to which was added a solution consisting of 2.8 liters of water and 386.4 g of silver nitrate dissolved therein, the solution being stirred in the dark for three hours. The reaction solution was filtered after cooling and the filtrations were repeated until the filtrate became transparent. After the concentration of the filtrate under a reduced pressure, 140.3 g of oxalic acid was added and the solution was allowed to stand overnight at a room temperature to obtain cis oxalate (trans 1 1,2-cyclohexanediamino) platinum (II) with a yield of 80% by means of the concentration under a reduced pressure. These experiments were repeated five times of which yields were 300 g, 280 g, 310 g, 290 g and 300 g.

The purity test for detecting the impurities contained in the cis-oxalate (trans-1 1,2-cyclohexanediamine) platinum (II) prepared in Example and Comparative Example was carried out by means of a high performance liquid chromatography (HPLC) method. The results are shown in Table 1.

The purity test was carried out in accordance with an absolute analytical curve method.

In other words, an analytical curve was prepared by stepwise introducing standard known amounts of the unreacted components supposed to be impurities, measuring the peak areas of the respective chromatograms and plotting the amounts of the components on the abscissa axis and the peak areas on the ordinate axis. The contents of the cis-oxalate (trans-1-1,2-cyclohexanediamine) platinum (II) in the samples respectively prepared in the above Example and Comparative Example were measured under the same conditions employing HPLC and calculated by determining the amounts of the components to be tested from the peak areas referring to the analytical curve.

The operation conditions of the chromatography were as follows.

TABLE 1

| Component | Relative Retention Time 'R | Purity Test, Content (%) | | Chromat. Condition |
| --- | --- | --- | --- | --- |
| | | Example | Comp. Example | |
| cis-oxalate (trans-1-1,2-cyclo-hexanediamine) platinum (II) | 1.00 | 100.0 | 98.0 | 1.2 |
| cis dichloro (trans-1-1,2-cyclo-hexanediamine) platinum (II) | 0.92 | 0 | 0.5 | 1 |
| cis-monochloro-monoaquo (trans-1-1,2-cyclohexane-diamine) platinum (II) | 0.87 | 0 | 0.3 | 2 |
| cis-diaquo (trans-1-1,2-cyclo-hexanediamine) platinum (II) nitrate | 0.82 | 0 | 0.3 | 3 |
| cis-diiodo (trans-1-1,2-cyclo-hexanediamine) platinum (II) | 1.73 | 0 | 0 | 2 |

Chromatography Operation Conditions 1:
Detector: Ultraviolet absorption photometer: 220 nm Column: Stainless tube having an inner diameter of about 4.6 mm and a length of 15 cm packed with octadecylsilicated silica gel having a particle size of 5 to 10 μm Column Temperature: 40° C.

Moving phase: Mixed solution of water and methanol (97:3)

Flow rate: 0.7 ml/min.

Chromatography Operation Conditions 2:

Moving phase: Mixed solution of water and methanol (85:15)

The other operation conditions were the same as those of Conditions 1.

Chromatography Operation Conditions 3:

Moving phase: Mixed solution of water and methanol (85:15)

The other operation conditions were the same as those of Conditions 1.

The purity test of silver impurities contained in the cis-oxalate trans-1-1,2-cyclohexanediamino) platinum (II) prepared above was carried out in accordance with an atomic absolute method. The results are shown in Table 2.

Operation Conditions of Atomic Absorption:
Employed gas:
Combustible gas: Acetylene
Combustion supporting gas Air
Lamp: Hollow silver cathode lamp
Wavelength: 328.1 nm.

TABLE 2

| Lot No. | Example | | Comparative Example | |
|---|---|---|---|---|
| | Silver (ppm) | Halogen (ppm) | Silver (ppm) | Halogen (ppm) |
| 1 | 0.3 | 2.2 | 31.6 | 5.0 |
| 2 | 0.6 | 3.5 | 1.3 | 28.2 |
| 3 | 0.9 | 2.2 | 36.2 | 7.3 |
| 4 | 0.3 | 2.9 | 0.9 | 65.3 |
| 5 | 0.7 | 2.2 | 25.4 | 10.3 |

The purity test was performed in accordance with a standard addition method. Three sample solutions were taken and a standard solution was added to each of the solutions in which the concentrations of the elements to be detected were stepwise distributed to which was added a solvent to make the volumes of the solutions identical. The absorption was measured for each of the solutions for plotting the amounts (concentrations) of the added standard element on the abscissa axis and the values of the absorption on the ordinate axis. The amount of the element to be detected (concentration of silver atom) was determined, after extending a regression line obtained by the plotting, by a distance between the intersecting point with the abscissa axis and the origin.

The concentration of halogen impurities was measured in accordance with a potentiometric titration method employing a flask in which oxygen burns. The results thereof are shown in Table 2.

Potentiometric titration employing flask in which oxygen burns
Flow rate of oxygen: 200 ml/min.
Flow rate of argon: 250 ml/min.
Temperature of electric furnace: 850° to 950° C.
Final Potential: 293 mV
Titration Current: 1.0 mA.

The halogen content was determined as chlorine concentration in accordance with the following equation.

Halogen content = Chlorine concentration (ppm) −

[Measured value (μg) × 1000]/[Sample amount (mg) ×

Recovery Rate]

As apparent from the Tables 1 and 2, no impurities were contained in the cis-oxalate (trans-1,1,2-cyclohexanediamino) platinum (II) prepared in Example.

What is claimed is:

1. A process of preparing a cis-platinum (II) complex of a 1,2-cyclohexanediamine isomer designated by a general formula (I)

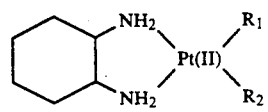

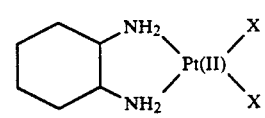

(in the formula, the conformation of 1,2-cyclohexanediamine is cis, trans-d or trans-l-isomer, and $R_1$ and $R_2$ form with each other a circular group selected from the group consisting of the formulae (V), (VI), (VII), (VIII), (IX) and (X))

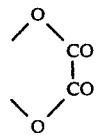

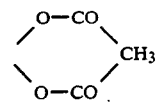

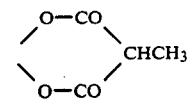

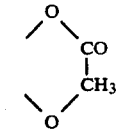

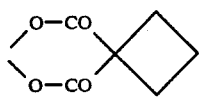

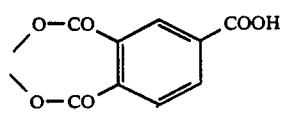

which comprises adding to a dihalogen compound of a cis-platinum (II) complex of a 1,2-cyclohexanediamine isomer designated by a general formula (II), wherein X is a halogen, a silver ion solution containing not less than two equivalents of silver in respect to the compound (II), removing silver chloride and/or silver bromide, adding to the solution sodium iodide and/or potassium iodide to convert the unreacted compound (II), the by-products of the compound (II) and an unreacted silver ion to their iodine compounds followed by the removal thereof and thereafter adding the corresponding organic dibasic acid of the formulae (V), (VI), (VII), (VIII), (IX) and (X) to the remaining platinum complex.

2. A platinum compound (I)

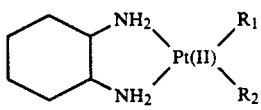   I

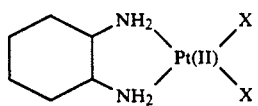   II (in the formula, the conformation of 1,2-cyclohexanediamine is cis, trans-d or trans-l-isomer, and $R_1$ and $R_2$ form with each other a circular group selected from the group consisting of the formulae (V), (VI), (VII), and (X))

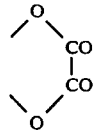   V

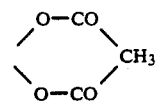   VI

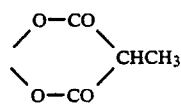   VII

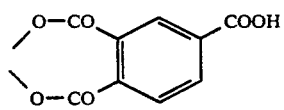   X substantially free from impurities prepared by reacting a dihalogen compound of a cis-platinum (II) complex of a 1,2-cyclohexanediamine isomer (II) with a silver compound to form silver iodide and/or silver bromide which is then removed, converting the unreacted compound (II), the by-products of the compound the corresponding organic dibasic acid of the formulae (V), (VI), (VII), and (X) and an unreacted silver to their corresponding iodine compounds by adding sodium iodide and/or potassium iodide which are then removed, and reacting the remaining platinum complex with an organic dibasic acid.

* * * * *

UNITED STATES PATENT AND TRADEMARK OFFICE
CERTIFICATE OF CORRECTION

PATENT NO. : 5,290,961
APPLICATION NO. : 08/003306
DATED : March 1, 1994
INVENTOR(S) : Koji Okamoto et al.

It is certified that error appears in the above-identified patent and that said Letters Patent is hereby corrected as shown below:

Col. 3, Lines 3-6, please delete "

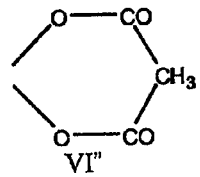

and insert --

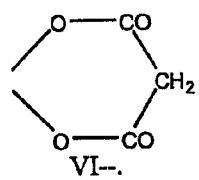

Claim 1, Col. 6, Lines 42-45, please delete "

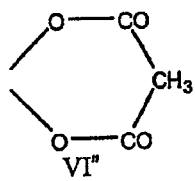

and insert --

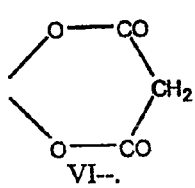

UNITED STATES PATENT AND TRADEMARK OFFICE
CERTIFICATE OF CORRECTION

PATENT NO. : 5,290,961
APPLICATION NO. : 08/003306
DATED : March 1, 1994
INVENTOR(S) : Koji Okamoto et al.

It is certified that error appears in the above-identified patent and that said Letters Patent is hereby corrected as shown below:

Claim 2, Col. 8, Lines 8 -11, please delete "

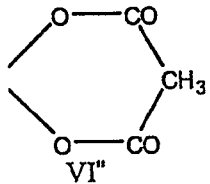

and insert --

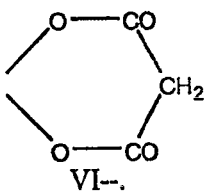

Claim 2, Col. 8, Line 25 of the text, please delete "(II)" and insert --designated by a general formula (II), wherein X is a halogen,--.

Claim 2, Col. 8, Lines 28-30 of the text, please delete "the corresponding organic dibasic acid of the formulae (V), (VI), (VII), and (X)" and insert --(II)--.

Claim 2, Col. 8, Lines 33-34 of the text, please delete "an organic dibasic acid." and insert -- the corresponding organic dibasic acid of the formulae (V), (VI), (VII), and (X).--.

Signed and Sealed this

Twenty-first Day of November, 2006

JON W. DUDAS
*Director of the United States Patent and Trademark Office*